United States Patent [19]

Cross, Jr. et al.

[11] 4,141,366
[45] Feb. 27, 1979

[54] LEAD CONNECTOR FOR TAPE ELECTRODE

[75] Inventors: Thomas E. Cross, Jr., Brooklyn Park; Douglas R. Gray, Anoka, both of Minn.

[73] Assignee: Medtronic, Inc., Minneapolis, Minn.

[21] Appl. No.: 852,849

[22] Filed: Nov. 18, 1977

[51] Int. Cl.² .............................................. A61N 1/04
[52] U.S. Cl. .................................................... 128/418
[58] Field of Search ............... 128/2.06 E, 2.1 E, 404, 128/410, 411, 416–418, DIG. 4

[56] References Cited

U.S. PATENT DOCUMENTS

| | | | |
|---|---|---|---|
| 3,547,105 | 12/1970 | Paine | 128/2.06 E |
| 3,565,059 | 2/1971 | Hauser et al. | 128/2.06 E |
| 3,607,788 | 9/1971 | Adolph et al. | 128/418 X |
| 4,008,721 | 2/1977 | Burton | 128/418 |

FOREIGN PATENT DOCUMENTS

| | | | |
|---|---|---|---|
| 2521697 | 12/1975 | Fed. Rep. of Germany | 128/2.06 E |
| 1564675 | 4/1969 | France | 128/2.06 E |

*Primary Examiner*—Lee S. Cohen
*Attorney, Agent, or Firm*—Schroeder, Siegfried, Ryan, Vidas & Steffey

[57] ABSTRACT

Electrical lead wire connection to a tape electrode is disclosed. Such electrodes are used for transmitting electrical signals through skin. The tape electrode includes a porous substrate material carrying a conductive layer comprised of finely divided silver metal suspended in a "dry" adhesive. An electrical lead wire is connected to the conductive layer of the tape electrode by a flat cover member having the same conductive layer on both sides thereof as is carried by the substrate of the tape electrode. One of the conductive layers of the cover member secures the lead wire to the conductive layer of the tape electrode. The other conductive layer of the cover member intimately contacts the skin along with the conductive layer of the tape electrode to provide for good electrical contact therewith when the tape electrode is applied thereto. The adhesive is normally "dry" and is activated at the time of application by a suitable solvent.

17 Claims, 4 Drawing Figures

U.S. Patent     Feb. 27, 1979     4,141,366
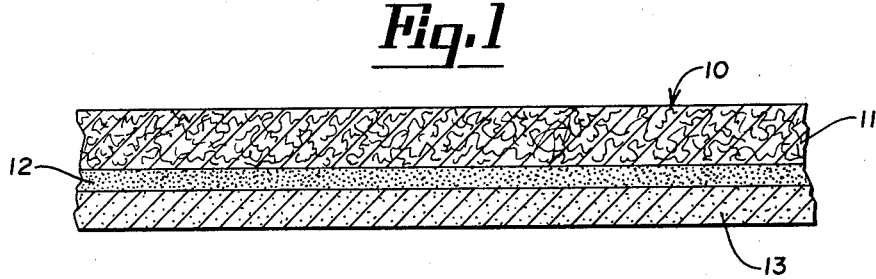
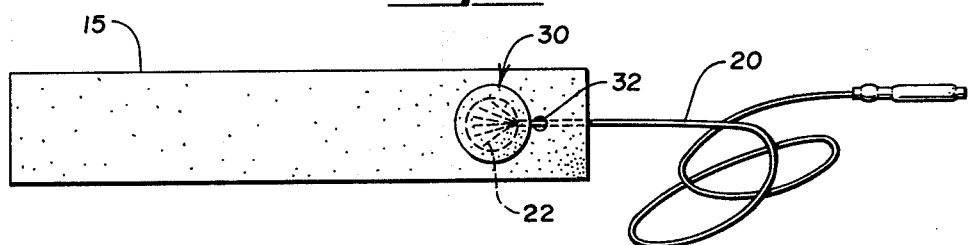
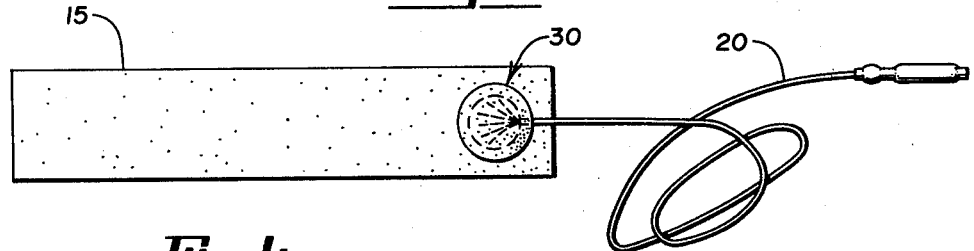
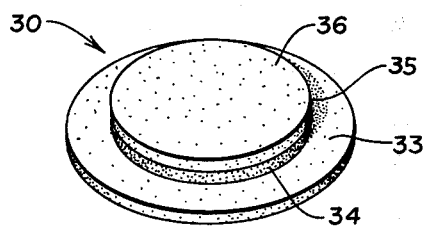

LEAD CONNECTOR FOR TAPE ELECTRODE

BACKGROUND OF THE INVENTION

This invention, in its preferred form, relates to tape electrodes for application to the outer layer of skin of the human body, particularly those capable of injecting electrical energy into the human body. More particularly, the invention provides an improved lead wire connector for such electrodes which permits long periods of usage and freedom of movement of the body when the electrode is in place.

When electrodes are utilized with devices, such as transcutaneous electrical nerve stimulators and the like which inject significant energy into the human body, as distinguished from monitoring electrodes, a number of factors must be considered. Such electrodes should be capable of remaining attached to the body for extended periods of time, such as several days, while allowing the subject wearing the electrode to engage in normal activities. In addition, the electrode must not encourage the growth of bacteria or other micro-organisms between the area of the electrode and the skin. Further, the electrode must be capable of distributing the transmitted electrical energy over a relatively broad area of the skin so as to avoid local energy concentrations, or "hot" spots which might cause discomfort to the subject. Finally, the electrode must be made of materials which are non-allergenic, must be easy to apply and must make good physical and electrical contact with both the electrial lead wire and the skin of the subject. One preferred type of tape electrode material for this purpose is described in the United States patent of Charles V. Burton, U.S. Pat. No. 4,008,721, dated Feb. 2, 1977 and entitled TAPE ELECTRODE FOR TRANSMITTING ELECTRICAL SIGNALS THROUGH THE SKIN, which patent is assigned to the present assignee hereof. Other types of electrodes of this kind have been described in the references cited in the aforementioned Burton patent and in U.S. patent application Ser. No. 674,176 filed Apr. 5, 1976, for TAPE ELECTRODE, now issued as U.S. Pat. No. 4,067,342 on Jan. 10, 1978 in the name of Charles V. Burton and assigned to the present assignee hereof.

When providing a means for connecting the electrical lead wire to the tape electrode, it must be borne in mind that the lead wire must make contact with the conductive side of the electrode and at the same time should not make direct electrical contact with the skin. In addition, the entire skin area beneath the electrode should receive substantially evenly distributed amounts of energy. Thus, any electrically "blank" spots on the conductive surface of the electrode are to be avoided.

SUMMARY OF THE INVENTION

In accordance with one preferred embodiment of this invention, there is provided a tape electrode for prolonged adhesion and re-adhesion, in event of loosening, to the skin. The electrode comprises a porous tape substrate carrying a conductive layer on one surface thereof comprising a mixture of skin-compatible metal particles blended into a water insoluble adhesive matrix in an amount sufficient to provide electrical continuity between the metal particles. The tape electrode includes means, according to the invention, for electrically joining a lead wire to the conductive layer of the tape. This means comprises a substantially flat cover member having two sides. One side is covered with substantially the same adhesive conductive coating as is carried by the tape substrate. The other side is at least partially preferably covered with the same adhesive conductive coating. The other side of the cover member is positioned with the conductive coating being over the lead wire with the coated layer of the substrate being below the lead wire. The cover member is then adherred to the layer on the substrate with the lead wire enclosed therebetween and in electrical contact with both the cover member and the conductive layer on the tape. The side of the cover member contacting the lead wire may be non-conductive if desired.

BRIEF DESCRIPTION OF THE DRAWINGS

A detailed description of one preferred embodiment of the lead wire connector for tape electrodes is hereafter described with specific reference being made to the drawings in which:

FIG. 1 is a side cross sectional view of a portion of a tape electrode of the prior art as may be used with the present invention;

FIG. 2 is a bottom view ie., a view of the adhesive side, of a tape electrode with a connector member according to the invention securing a lead wire thereto in which the insulated portion of the lead wire extends through the tape electrode;

FIG. 3 is a bottom view ie., a view of the adhesive side, of a tape electrode with a connector member according to the invention securing a lead wire thereto in which the insulated portion of the lead wire extends along the conductive surface of the tape electrode; and FIG. 4 is a perspective view of a preferred cover member according to the invention for securing a lead wire to a tape electrode.

DESCRIPTION OF THE PREFERRED EMBODIMENTS

In FIG. 1 there is illustrated, in cross section, a tape electrode 10 of the type described in the aforementioned Burton patent. Tape electrode 10 consists of a porous backing material or substrate 11, a conductive layer 13 carried on one side thereof and held thereto by a layer 12 of adhesive material.

Substrate 11 is preferably a thin, flexible, porous, cloth-like material through which water in either gas or liquid form can pass. The passage of water through this material is essential in order that moisture generated by the wearer may pass from the skin through the tape electrode 10 to minimize the possibility of lifting the electrode from the skin after prolonged usage. A non-woven rayon fiber material has been found to be satisfactory for this purpose.

While several types of adhesive may be selected, the adhesive material of layer 12 is preferably an acrylic copolymer adhesive such as is commonly used in medical tapes. One such acrylic copolymer which may be used is available from National Starch Co. under their designation Resin 30-1289. This material is a vinyl acrylic copolymer in an organic solvent. Layer 12 is as thin as possible while still providing total coverage of the surface of substrate 11. Its purpose is to provide a surface for the application of the active electrode layer 13 to substrate 11. Vinyl acrylic copolymer may be used in layer 12. They are relatively permeable to moisture and permit the passage therethrough of any perspiration generated during normal periods of wearing. It should be appreciated that the combination of substrate 11 and adhesive layer 12 is commercially available from the 3M company of St. Paul, Minnesota under the trademark name MICROPORE surgical tape.

Coating layer 13, which is electrically conductive, is a mixture of adhesive material blended with a quantity of finely divided silver metal in sufficient quantities to make layer 13 electrically conductive. Other skin compatible metals such as gold or platinum may be used but silver is preferred. The particles of silver metal preferably are very small and are blended with the adhesive. The adhesive used in conductive layer 13 is preferably an acrylic copolymer of the same type as used in layer 12. The silver particles are preferably of the type which may be conveniently obtained from Handy and Harmon under their designation Silflake 135. This silver is in flake form and retains its metallic appearance. A suitable blend for the conductive coating of layer 13 is in the ratio of 10 grams of silver blended with 3 grams of copolymer adhesive material. While higher quantities of silver relative to the copolymer may be utilized, this results in a commensurately higher cost per unit area of the electrode. Somewhat lower quantities of silver may be utilized commensurate with an increased volume resistivity. In the ratio indicated, the volume resistivity will be less than about 1 ohm-centimeter. The composite material will be in an essentially non-tacky condition.

The metal-adhesive composite may be applied to layer 12 to form layer 13 by incorporation of a suitable fluidizing solvent, such as toluene or acetone, into a quantity of the composite. The fluidized composite may then be applied to layer 12, as by rolling, to form layer 13. Alternatively, layer 13 may previously have been formed on a backing sheet such as polyethylene coated paper, and following the application of the solvent thereto, the combination of layers 11 and 12 may be placed in contact with layer 13. In either case, upon evaporation of the solvent, a dry finished tape electrode 10 exists. The backing for layer 13, if used, may be left on the finished product for protection of the conductive layer until use of tape electrode 10 is desired. At this time, it is merely necessary to peel away the backing strip in the known manner. In addition, the backing may act as a separator to allow the tape to be rolled after manufacture.

The thickness of conductive layer 13 should preferably be as low as possible, yet still maintain electrical continuity across the tape surface. It has been found that layer 13 is preferably less than 5 mils in thickness and normally on the order of about 2-3 mils.

Layer 12 may be on the order of about 1 mil in thickness. Layer 12 may be eliminated and conductive layer 13 applied directly to the substrate 11. However, this has the disadvantage that some of the conductive material may soak through substrate 11 and thereby render the top, or nonconductive side, thereof conductive. The advantage, however, of eliminating layer 12 is a cost saving.

The lead wire connector, according to the invention, for these tape electrodes is shown in FIGS. 2 and 3. For exemplary purposes, a strip electrode 15, which may be of varying lengths, is shown. Strip 15 may, for example, have a length of six inches and a width of approximately one inch. A stranded electrical lead wire 20 has the insulation removed from one end to expose the wire 22, indicated in phantom. The exposed wire 22 is secured to the conductive surface of the strip electrode 15 approximately ¾ inch from one end through a cover member 30. As indicated in FIG. 2, lead wire 20 may be directed through an aperture 32 in tape 15 with the exposed wire 22 positioned between cover 30 and the conductive surface of strip electrode 15. In an alternate embodiment, shown in FIG. 3, lead wire 20 may be directed under the conductive surface of strip electrode 15 from one side thereof with cover member 30 being positioned over the exposed wire 22. Preferably, cover member 30 and exposed wire 22 are located approximately ¾ inch from an end of the strip electrode 15.

A preferred form of cover member 30 is shown in enlarged perspective view in FIG. 4 as being formed of two pieces of the tape electrode material with the backing or substrate sides positioned toward one another and the conductive sides being positioned away from one another. Thus, in FIG. 4, cover member 30 as shown includes a large disc 33 of the tape electrode material 10 approximately ¾ inch in diameter, a small disc 34 of double-sided adhesive coated tape material approximately ½ inch in diameter positioned in the center of the nonconductive side of disc 33, and a disc 35 of the tape electrode material 10 of the same diameter as the double coated tape disc 34 positioned with the nonconductive side thereof being affixed to double coated tape disc 34. The double coated tape 34 is preferably as thin as possible and may be Double Coated Medical Tape No. 1522 manufactured by the 3M Company of St. Paul, Minnesota.

Cover member 30 is positioned over the exposed wires 22 of lead wire 20 with the conductive surface 36 of disc 35 bearing against the conductive surface of the tape strip 15. Heat sealing is applied by means of a pair of heat plates to clamp surface 36 of cover member 30 against the exposed wires 22 and conductive surface of tape strip 15 to secure the same thereto. This arrangement makes direct electrical and physical contact between the conductive surfaces 36 of cover member 30 and the conductive surface of tape strip 15 and thereby secures the lead wire to tape strip 15. Thus, the user may wear the tape electrode over extended periods without causing the lead wire to be broken or disconnected and without destroying the electrical condutivity to the tape strip.

This particular arrangement eliminates the flex points which may otherwise be present in tape electrodes and thereby reduces the instance of tape fracture due to lead connection.

If desired, the double coated tape may be eliminated and a suitable adhesive applied to the facing nonconductive surfaces of the tape material discs 33 and 35 to cause the same to adhere to one another and to form cover member 30. In addition, a single substrate material may be coated on both sides in the manner described with respect to FIG. 1 in making the tape electrode 10 to provide cover member 30.

Another manner of fabricating cover member 30 is to make layer 35 from the copolymer without the metal or even eliminate layers 34 and 35 entirely. This saves the cost of the metal in that layer but results in a physical contact which is not as strong. An electrode with this configuration may nevertheless be useful with patients with little movement, such as patients recovering from surgery upon whom the electrode is placed.

The improved tape electrode 15 with attached cover member 30 is readily applied to the human body by swabbing the area of the skin surface, to which the tape electrode is to be applied, with a solvent, such as acetone or alcohol, thereby washing excess body oils therefrom. The conductive sides of strip electrode 15 and cover member 30 are then coated with the solvent to partially fluidize the adhesive thereon and give it a high tack and wetting capability relative to the human skin. In this condition, the conductive layer readily penetrates into the intracacies of the human skin to provide good physical and electrical contact. In addition, when the adhesive layers are fluidized, the exposed conductive surface of cover member 30 and the conductive surface of the strip electrode 15 flow together and thereby create a continuous electrically conductive layer. Thus, no electrically blank spots appear on the conductive surface of strip electrode 15 and cover member 30 and complete electrical contact is achieved with the skin.

The improved tape electrode 15, made of water insoluble materials, has a low thickness which permits transmission of water vapor thereacross so there is less tendency for the electrode to loosen or flake off after prolonged attachment. At the same time, it is readily re-adherable to the skin by applying the solvent to the surface of tape electrode 15 should it loosen. The attachment of the lead wire 20 to tape electrode 15 is such that it is securely positioned thereon and permits the wearer normal daily movement without loosening the electrode or destroying the electrical connection. Tape electrode 15 is readily removed by merely grasping the electrode and peeling it off the skin. Any residual adhesive or silver may be loosened or washed away with the same solvent.

In considering this invention it should be remembered that the present disclosure is illustrative only and the scope of the invention should be determined by the appended claims.

What we claim is:

1. A tape electrode for adhesion to the skin, comprising:
    a porous substrate;
    a layer of conductive material and an adhesive matrix carried on one side of said substrate;
    lead means contacting said conductive layer for connecting said conductive layer to an electrical apparatus; and
    cover means of a substantially flat shape and having two sides, at least one of which is coated with conductive material, said cover means being positioned on said conductive material layer of said substrate so that said lead means is between said cover means and said layer of conductive material on said substrate with the coated side of the cover means member disposed away from the lead means.

2. The invention according to claim 1 wherein the various named conductive materials are all capable of being fluidized to a tacky condition upon the application thereto of a solvent.

3. The invention according to claim 2 wherein said coating of conductive material on said cover means electrically contacts said conductive layer on said substrate.

4. The invention according to claim 1:
    wherein said conductive materials are a mixture of skin compatible metal particles blended into a water insoluble, low tack adhesive matrix in an amount sufficient to provide electrical continuity between the metal particles.

5. The invention according to claim 4 wherein the said conductive materials are at least partially soluble in nonaqueous solvent.

6. The invention according to claim 4 wherein said adhesive matrix of said conductive materials are non-toxic, non-irritating and non-allergenic polymers which are at least partially soluble in non-acqueous solvent.

7. The invention according to claim 1 including a coating of conductive material on both side of said cover means.

8. A tape electrode for prolonged adhesion to the skin and re-adherable thereto through the use of a solvent, comprising:
    a porous tape substrate;
    a conductive coating on one surface of the tape substrate having a mixture of skin compatible metal particles blended into a water insoluble, low tack adhesive matrix in an amount sufficient to provide electrical continuity between the metal particles;
    a lead wire; and
    means electrically joining said lead wire to the conductive coating on the tape substrate, said means including a substantially flat cover member having two sides, one of which is coated with a conductive material and the other of which is at least partially coated with a conductive material, said other side of said cover member being positioned with said at least partial coating of conductive material in conductive contact with the lead wire and holding it against the conductive coating on the tape substrate.

9. The tape electrode of claim 8 wherein said adhesive matrix of said conductive coating is a non-toxic, non-irritating and non-allergenic polymer which is at least partially soluble in liquid solvent.

10. The invention according to claim 9 wherein the solvent referred to is of the nonaqueous type.

11. A tape electrode for prolonged adhesion to the skin and re-adherable thereto through the use of a liquid non-aqueous solvent, comprising:
    a porous tape substrate;
    a conductive coating on one surface of the tape substrate having a mixture of skin compatible metal particles blended into a water soluble, low tack adhesive matrix in an amount sufficient to provide electrical continuity between the metal particles, the adhesive matrix being a non-toxic, non-irritating and non-allergenic polymer which is at least partially soluble in liquid non-aqueous solvent;
    a lead wire, and
    means electrically joining said lead wire to the conductive coating on the tape substrate, said means including a substantially flat cover member comprised of two pieces of porous tape substrate having a conductive coating on one side of each thereof and a double adhesive coated tape positioned between the other sides of said two substrates, the conductive coating on one side of one of said two substrates covering the entire side thereof, the other of said two sides being at least partially covered with the conductive coating, said other side of said two sides being positioned with said at least partial conductive coating in conductive contact with the lead wire and holding it against the conductive coating on the porous tape substrate.

12. The tape electrode of claim 11 in which the cover member is formed as a disc in which one of said pieces of tape substrate forming the cover member is of a lesser diametrical dimension than the other and in which the piece of lesser diametrical dimension contacts the lead wire and said conductive coating on the one surface of the tape substrate and secures the cover member and the lead wire to said conductive coating on the one surface of the tape substrate.

13. The tape electrode of claim 12 in which the lead wire extends through an aperture in the tape substrate and the conductive coating on the surface thereof, extending from the other surface of the same to be secured by the cover member to the conductive coating.

14. The tape electrode of claim 11 in which the lead wire extends along the conductive coating on the surface of the tape substrate and between it and the cover member with bare wires thereof secured by the cover member to the conductive coating on the surface of the tape substrate.

15. A tape electrode for prolonged adhesion to the epidermal skin of a human and readherable with application of a nonaqueous solvent to the free side thereof, the tape electrode comprising:
   a strip of porous tape substrate having a conductive coating on one surface of the tape surface, which coating includes a mixture of skin compatible metal particles blended into a water insoluble, low tack adhesive matrix, the amount of metal particles in said matrix being sufficient to provide electrical continuity between the particles and the adhesive matrix being non-toxic, non-irritating and non-allergenic polymer at least partially soluble in a volatile organic solvent;
   a lead wire having a portion thereof adapted for contacting the conductive coating on the tape substrate; and
   a cover member contacting the conductive coating on the tape substrate with the lead wire portion therebetween and securing said portion of the lead wire to the conductive coating of the tape substrate under the cover member, said cover member being formed of two substrate-to-substrate pieces of the same material as the tape substrate, the two substrate-to-substrate pieces comprising: an inner piece in contact with the conductive coating of the tape substrate and holding the portion of the lead wire between itself and the conductive coating of the tape structure and an outer piece including a conductive coating of adhesive material on the outermost surface thereof, the inner piece having at least an adhesive material on the surface contacting the lead wire and conductive coating of the tape substrate.

16. A tape electrode for adhesion to the skin comprising:
   a tape substrate;
   a conductive coating on one surface of the tape substrate having a mixture of skin compatible metal particles blended into a low tack adhesive matrix in an amount sufficient to provide electrical continuity between the metal particles;
   a lead wire; and
   means electrically joining said lead wire to the conductive coating on the tape substrate, said means including a substantially flat cover member having two sides, one of which is covered with a coating of conductive material and the other of which is at least partially coated with a conductive material, said other side of said cover member being positioned with said at least partial coating of conductive material in conductive contact with the lead wire and holding it against the conductive coating on the tape substrate.

17. The tape electrode of claim 16 wherein said cover member comprises two pieces of tape substrate with the conductive materials carried on one side of each thereof and a double coated adhesive tape positioned between the other sides of said substrates.

* * * * *

UNITED STATES PATENT AND TRADEMARK OFFICE
CERTIFICATE OF CORRECTION

PATENT NO. : 4,141,366
DATED : February 27, 1979
INVENTOR(S) : Thomas E. Cross, Jr. and Douglas R. Gray It is certified that error appears in the above-identified patent and that said Letters Patent are hereby corrected as shown below:

IN THE CLAIMS

Column 5, line 49, delete "member".

Column 6, line 4, delete "side" and insert --sides-- therefor.

Column 7, line 19, delete "surface" second occurance and insert --substrate-- therefor.

Column 8, line 5, delete "structure" and insert --substrate-- therefor.

Signed and Sealed this

Twenty-sixth Day of June 1979

[SEAL]

Attest:

RUTH C. MASON
Attesting Officer

DONALD W. BANNER
Commissioner of Patents and Trademarks